US00PP20003P2

(12) United States Plant Patent
Cho

(10) Patent No.: US PP20,003 P2
(45) Date of Patent: May 19, 2009

(54) ***COLOCASIA* PLANT NAMED 'BLUE HAWAII'**

(50) Latin Name: *Colocasia esculenta*
Varietal Denomination: BLUE HAWAII

(76) Inventor: John Cho, 424 Mauna Pl., Kula, HI (US) 96790

( * ) Notice: Subject to any disclaimer, the term of this patent is extended or adjusted under 35 U.S.C. 154(b) by 0 days.

(21) Appl. No.: 12/006,576

(22) Filed: Jan. 4, 2008

(51) Int. Cl.
*A01H 5/00* (2006.01)

(52) U.S. Cl. ..... Plt./373

(58) Field of Classification Search ..... Plt./373
See application file for complete search history.

*Primary Examiner*—S. B McCormick Ewoldt

(57) ABSTRACT

A new cultivar of cultivar of *Colocasia* plant named 'BLUE HAWAII' that is characterized by a combination of large green leaves with prominent bluish purple veins, undulating bluish purple margin, a matte finish and semi-glossy burgundy colored petioles. In combination these characteristics distinguish 'BLUE HAWAII' from all other varieties of *Colocasia* known to the inventor.

5 Drawing Sheets

Genus: *Colocasia.*
Species: *esculenta.*
Denomination: 'BLUE HAWAII'.

BACKGROUND OF THE INVENTION

The present invention relates to a new and distinct variety of *Colocasia* commonly known as the taro plant or elephant ears. *Colocasia* is grown as a food crop or for use as an ornamental for container or the landscape. The new cultivar is known botanically as *Colocasia esculenta* and will be referred to hereinafter by the cultivar name 'BLUE HAWAII'. 'BLUE HAWAII' is one of is one of five co-pending applications by the inventor relating to new cultivars of *Colocasia.* The other four co-pending applications are titled *Colocasia* plant named 'Hawaiian Eye' (U.S. application Ser. No. 12/006,580), *Colocasia* plant named 'Hilo Bay' (U.S. application Ser. No. 12/006,474), *Colocasia* plant named, 'Diamond Head' (U.S. application Ser. No. 12/006, 579), and *Colocasia* plant named 'Pineapple Princess' (U.S. application Ser. No. 12/006,581).

*Colocasia* is a tuberous rooted perennial which is native to tropical Asia and Polynesia. It grows to 1.5–2 m in height from starchy tubers. The leaves of *Colocasia* are heart-shaped and very large in size. The tuberous roots are cooked and eaten as a starchy staple in many tropical areas. It is also grown as ornamental plants for the landscape in warmer climates or as a container plant in colder areas.

The new *Colocasia* variety named 'BLUE HAWAII' is the product of a formal breeding program carried out in a cultivated area in Kula, Hi. The purpose of the breeding program is to develop new commercial varieties by combining attributes not found in currently commercially available varieties.

'BLUE HAWAII' is a seedling selection from the controlled pollination between the female parent breeding line '2001-52' (not patented) and male parent breeding line '2002-41' (not patented). Initially designated as '2005-24', 'BLUE HAWAII' was derived from a single plant selected in 2005.

The new variety 'BLUE HAWAII' has large green colored matte finish leaves with prominent bluish-purple colored venation and a bluish-purple undulating leaf margin. 'BLUE HAWAII' produces uniform dark burgundy colored petioles when mature; young petioles are green to light burgundy in color. The leaves are ⅓ to ½ times larger than its female and male parents. The male parent, '2002-41', exhibits greenish-purple colored leaves with a matte finish a smooth margin, and light purple venation. The petioles are dark purple in color with a matte finish. The female parent, '2001-52' exhibits smaller violet leaves with a purple spot on the upper leaf surface at the point of leaf and petiole attachment and an undulating margin. The petioles are of a dark purple in color. In these aspects, this new variety differs from its parents.

The closest comparison variety known to the inventor is 'Violet Stem' (not patented), its closest commercial variety. 'BLUE HAWAII' produces large green colored matte finish leaves with prominent bluish-purple colored venation and a bluish-purple undulating leaf margin compared to 'Violet Stem' that produces long green leaves with a slight hazy purple cast. 'BLUE HAWAII' produces uniform semi-glossy, dark burgundy colored petioles when mature compared with the deep purple colored petioles of 'Violet Stem'. 'BLUE HAWAII' produces secondary lateral shoots that are closely attached to the mother plant as compared with 'Fontanesii' (not patented) that produces secondary lateral shoots on long stolons.

The most commonly employed means of asexual propagation of the genus *Colocasia* is the excision and replanting of a plant shoot which consists of the apical 1 cm–2 cm portion of the plant corm with the attached basal 15 cm–20 cm portion of the petiole. In regions of the world where *Colocasia* is grown, this plant shoot is known as a "huli", and the means of propagation is known as "huli propagation". Asexual propagation of hulis of 'BLUE HAWAII' began in 2005 in Hawaii by the inventor using huli propagation whereby the apical shoots are separated from the plant by cutting the shoot at the top of the corm immediately above the newest leaf scar and planted. Evaluation in field and pot studies have shown the unique features of 'BLUE HAWAII' to be stable, uniform, and reproduces true to type in successive generations of asexual propagation.

SUMMARY OF THE INVENTION

The following traits have been repeatedly observed and represent the distinguishing characteristics of the new *Colocasia* variety named 'BLUE HAWAII'. In combination these traits set 'BLUE HAWAII' apart from all other varieties of *Colocasia* known to the inventor. 'BLUE HAWAII' has not been tested under all possible conditions and phenotypic differences may be observed with variations in environmental, climatic and cultural conditions, however, without any variance in genotype:

1. 'BLUE HAWAII' exhibits large saggitate-shaped green colored leaves with prominent bluish-purple colored venation and a bluish-purple undulating leaf margin.
2. The surface of the leaves of 'BLUE HAWAII' is a matte finish.
3. 'BLUE HAWAII' produces uniform dark burgundy colored petioles when mature.

BRIEF DESCRIPTION OF THE DRAWINGS

The accompanying color drawings

Figure 1:
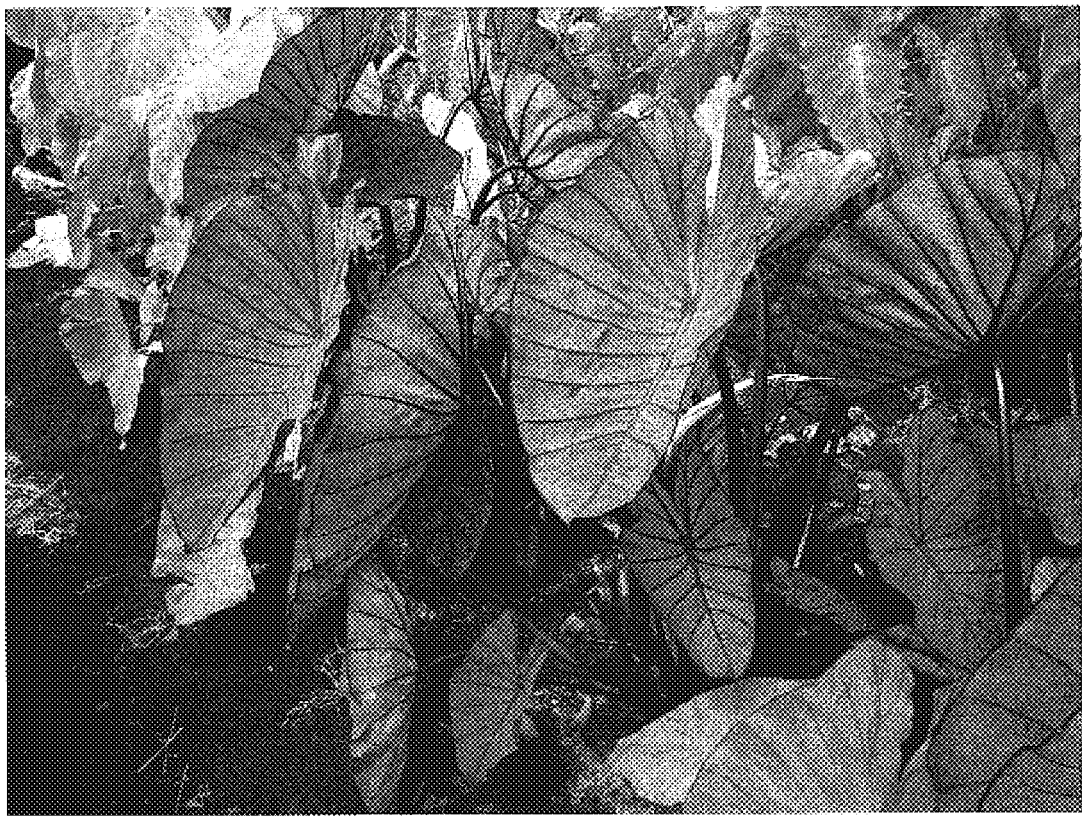
FIGS. 1 to 5 illustrate the overall appearance of 'BLUE HAWAII' showing the colors as true as it is reasonably possible to obtain in colored reproductions of this type. Colors in the drawing may differ from the color values cited in the detailed botanical description, which accurately describe the actual colors of the new variety 'BLUE HAWAII'.

The drawing labeled as FIG. 1 shows 'BLUE HAWAII' grown from a huli after approximately 3 months.

Figure 2:
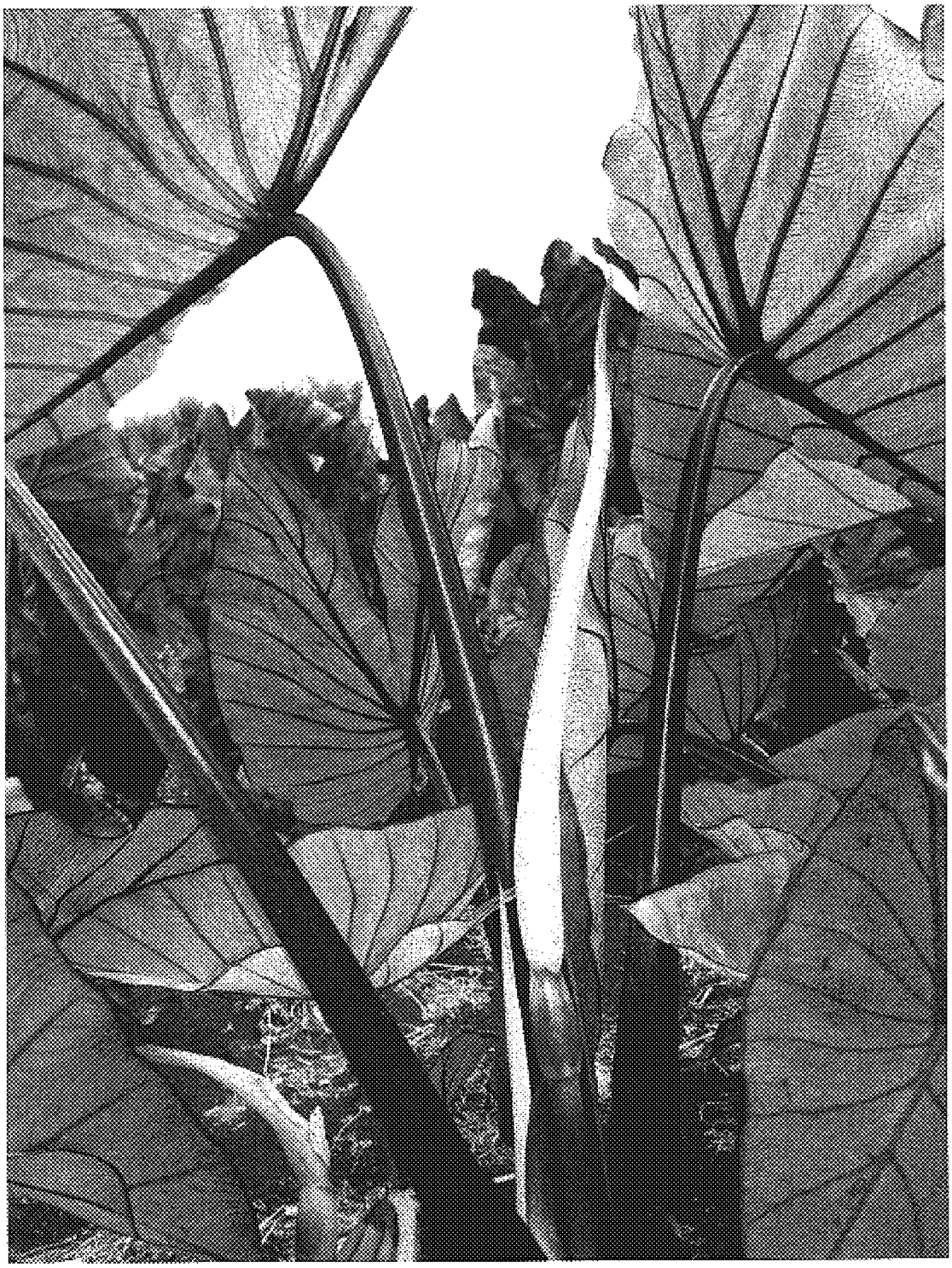

The drawing labeled as FIG. 2 shows the semi glossy burgundy colored petioles of 'BLUE HAWAII'. The drawing also shows the sheath or spathe that normally encloses the inflorescence or spadix.

Figure 3:
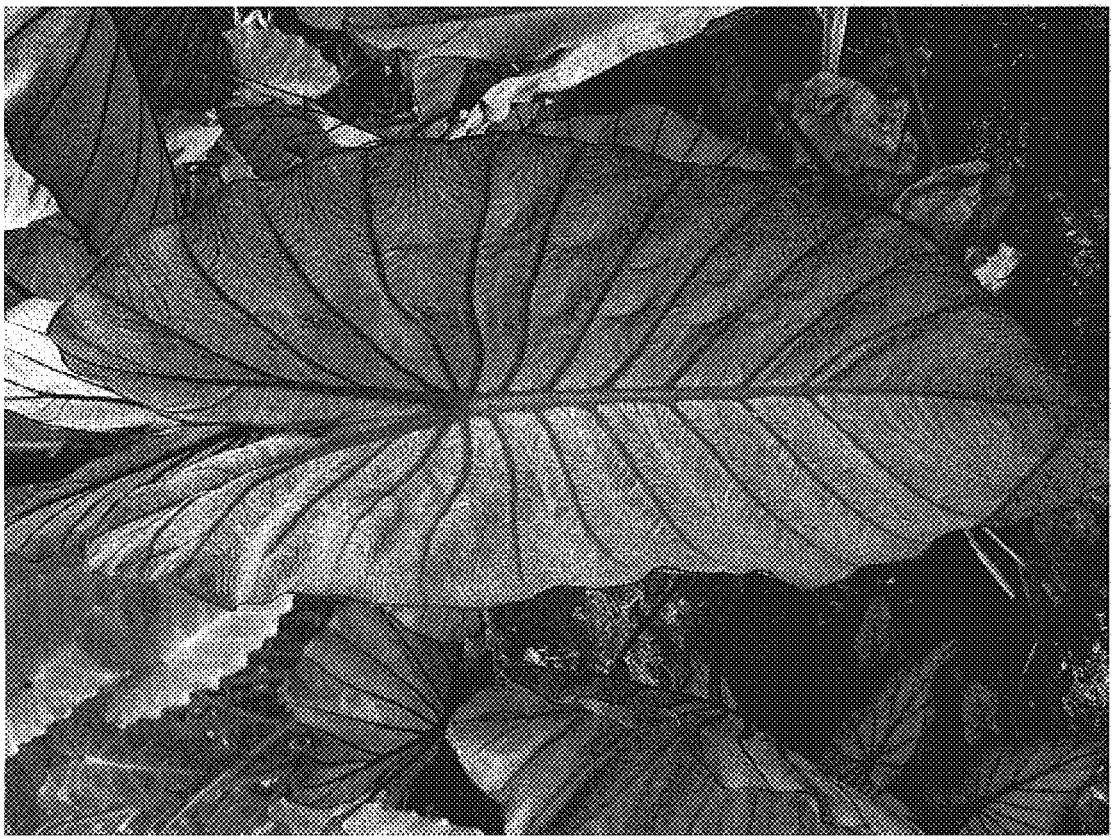

The drawing labeled FIG. 3 illustrates a sagittate 'BLUE HAWAII' mature leaf blade with prominent bluish-purple venation and undulating bluish-purple margin. Lamina is green with a matte fish. This drawing also illustrates that part of the leaf which is known as the "piko" namely the area of upper leaf surface which is present at the junction of the leaf blade with the petiole and from which three principal veins radiate.

Figure 4:
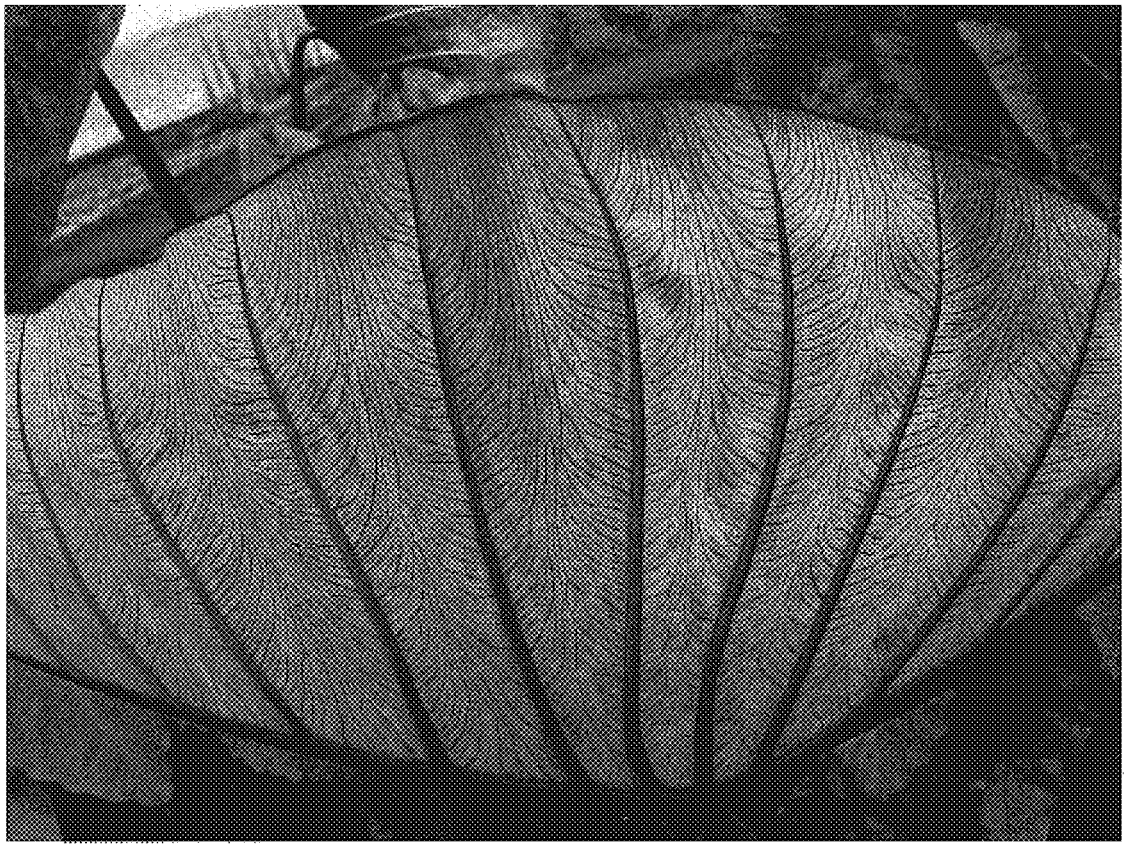

The drawing labeled as FIG. 4 shows the underside of a mature leaf of 'BLUE HAWAII' with light green lamina and purple primary and secondary venation.

Figure 5:
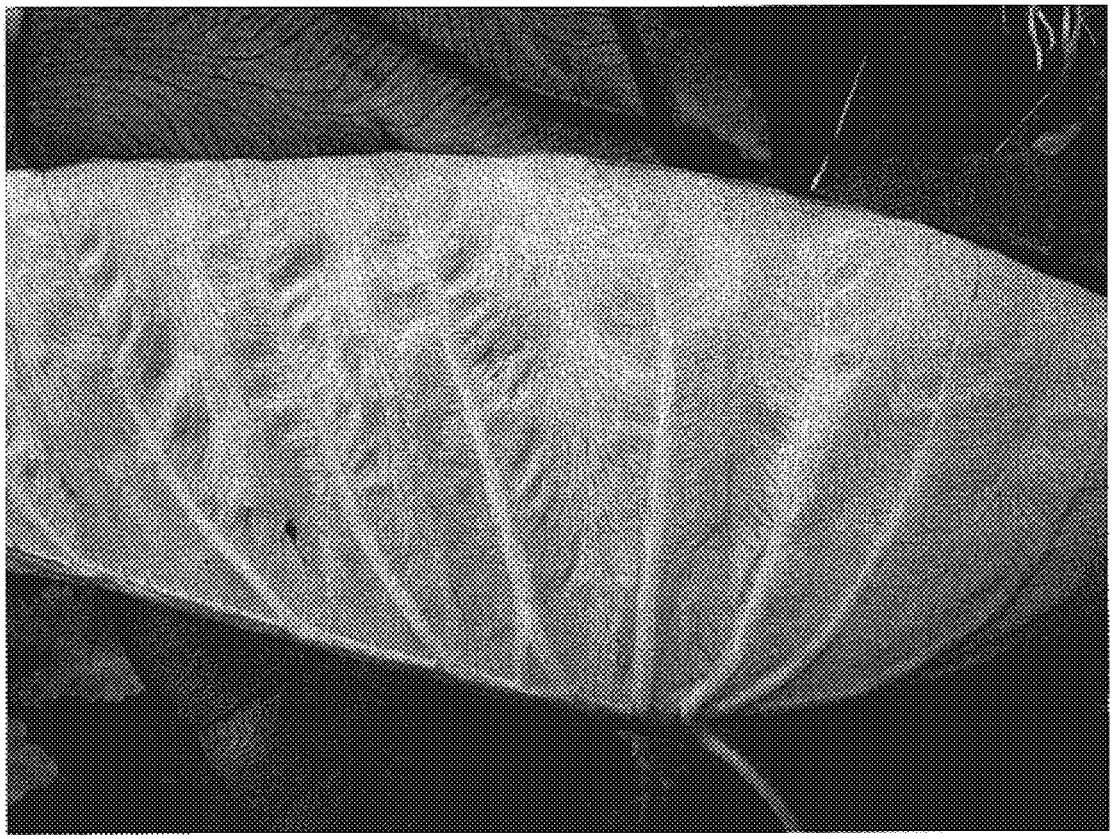

The drawing labeled as FIG. 5 shows the underside of a young recently unfurled leaf of 'BLUE HAWAII' with light green lamina and light purple primary venation. All drawings have been made from plants which were approximately 3 months old from a division and which have been grown out-of-doors. No growth regulators have been applied.

BOTANICAL DESCRIPTION OF THE PLANT

The following is a detailed description of the new *Colocasia* plant named 'BLUE HAWAII'. Data was collected from plants that were 3–6 months of age grown outside in Kula, Hi. as indicated. The color determinations are in accordance with the 2001 edition of the Royal Horticultural Society Colour Chart, London, England, except where general color terms of ordinary dictionary significance are used. The growing requirements are similar to other *Colocasia*.

Botanical classification:
Genus: *Colocasia.*
Species: *esculenta.*
Denomination: 'BLUE HAWAII'.
Common name: Taro or elephant ears.
Plant use: Food, container or landscape plant.
Cultural requirements: Cultural requirements are well draining soil or growing media, full sun to partial shade.
Root system: Fibrous.
Plant vigor: Vigorous.
Parentage:
*Female parent.*—'2001-52'.
*Male parent.*—'2002-41'.
Plant description: The plant has 4–6 suckers closely attached to the mother plant. A "mother plant" is the plant material which is first introduced into the soil to begin production. Typically, this plant material contains part of the huli and 2–3 leaf blades. This produces a "mother corm" which produces lateral shoots called 'cormels' which give rise to daughter plants. Daughter plants begin to appear above soil level about 2–3 months after planting of the mother plant.
Plant dimensions: 106 cm to 127 cm in height and 96.5 cm to 134.5 cm in width.
Plant hardiness: USDA Zone 7b.
Propagation: Propagation is accomplished by huli propagation and by tissue culture.
Huli Propagation: Root formation occurs immediately after transplanting. Propagation is complete when fully rooted. Daughter plants appear above soil level around 2–3 months after huli planting.
Tissue Culture: time to develop a new plant capable of growing on its own roots: 3 weeks.
Crop time (from propagation to a saleable 1 gallon container): 6–10 weeks at temperatures of 75 degrees Fahrenheit–65 degrees Fahrenheit. Pest or disease susceptibility and resistance: No more or less susceptible to disease or pests than other cultivars.
Tuberous roots:
*Dimensions.*—7.0 inches in length, 3.3 inches in diameter.
*Color.*—155B.
Foliage:
*Number.*—On average, a 5 to 6 month old mother plant maintains 5 functional leaves at a time, each new leaf is produced approximately every 10 days until the corm matures.
*Petioles.*—Length: Up to 105 cm in length. Width: 11.5 mm (just below attachment to lamina)×21.5 mm (at the upper sinus)×36 mm (at the middle of the sinus) Color: N186C. Sap color: Colorless.
*Leaf.*—Dimensions at maturity (5–6 months old): 675 mm in length and 435 mm in width. Aspect: Erect with apex down. Shape: Sagittate lamina. Margins: Entire, slightly undulating. Apex: Pointed. Base: Peltate. Lamina appendages: Absent. Attachment: Petiolate with characteristic tissue formed at junction of leaf blade with the upper termination of the petiole. This area of the leaf tissue is also known as the "piko" and is evident by virtue of its upper surface being the same color as the veins or darker. The principal veins radiate from the piko. Piko Color: N186A merging into the laminar venation. Leaf sheaf: Open. Texture: Matte. Leaf color (adaxial surface): 144A. Leaf color (abaxial surface): 144A. Venation: Palmate. Veins: Three principal veins radiating from the piko. The largest a midrib extending from the piko to the tip of the lamina with up to 12 pairs of secondary veins radiating from it. Vein color (adaxial surface): N186A. Vein color (abaxial surface): slightly N186D when young becoming darker N186D at maturity.

Flowers and reproductive organs: The inflorescence arises from the leaf axils. The inflorescence is made up of a short peduncle, a spadix, and spathe. The spadix is botanically a spike, with a fleshy central axis to which the small sessile flowers are attached. The spadix is 105 mm to 120 mm long, with female flowers at the base, male flowers towards the tip, and sterile flowers in between, in the region compressed by the neck of the spathe. The extreme tip or appendage of the spadix has no flowers at all. The spathe is a large yellowish bract, 240 mm to 330 mm long, which sheathes the spadix. The lower part of the spathe is green (144C) in color and wraps tightly around the spadix and completely occludes the female flowers from view. The top portion of the spathe is yellow (13B) in color and is rolled inward at the apex, but is open on one side to reveal the male flowers on the spadix. The top and bottom portions of the spadix are separated by a narrow neck region, corresponding to the region of the sterile flowers on the spadix.

Seed: Seed is not produced naturally since male and female flowers within each inflorescence do not mature at the same time. Pollination can be achieved manually or in nature, only with the presence of small insect pollinators which are found in regions of genetic origina of the species, and not Hawaii.

It is claimed:

1. A new and distinct cultivar of *Colocasia* plant named 'BLUE HAWAII' as described and illustrated herein.

* * * * *

UNITED STATES PATENT AND TRADEMARK OFFICE

CERTIFICATE OF CORRECTION

PATENT NO. : PP20,003 P2
APPLICATION NO. : 12/006576
DATED : May 19, 2009
INVENTOR(S) : John Cho It is certified that error appears in the above-identified patent and that said Letters Patent is hereby corrected as shown below:

On Column 1, line 1, please insert the following header and paragraph:

--Statement of Government Interest

This invention was made with Government support under Grant No. 2001-31100-06015/HAW914H awarded by the U.S. Department of Agriculture. The Government has certain rights in this invention.--

Signed and Sealed this
Twenty-second Day of November, 2011

David J. Kappos

David J. Kappos
*Director of the United States Patent and Trademark Office*